United States Patent [19]
Edwards

[11] Patent Number: 6,036,688
[45] Date of Patent: Mar. 14, 2000

[54] RADIO FREQUENCY REFRACTIVE KERATECTOMY APPARATUS AND METHOD

[76] Inventor: Stuart D. Edwards, 658 Westridge Dr., Portola Valley, Calif. 94028

[21] Appl. No.: 09/098,598

[22] Filed: Jun. 17, 1998

[51] Int. Cl.[7] .................................................. A61B 17/39
[52] U.S. Cl. ............................... 606/34; 606/41; 606/50; 607/99
[58] Field of Search ................................ 606/34, 41, 49, 606/50; 607/99

[56] References Cited

U.S. PATENT DOCUMENTS

| | | | |
|---|---|---|---|
| 4,326,529 | 4/1982 | Doss et al. | 128/303.1 |
| 4,381,007 | 4/1983 | Doss | 128/303.1 |
| 5,025,811 | 6/1991 | Dobrogowski | 606/41 |
| 5,174,304 | 12/1992 | Latina et al. | 606/41 |
| 5,749,871 | 5/1998 | Hood et al. | 606/41 |

*Primary Examiner*—Lee Cohen
*Attorney, Agent, or Firm*—Flehr, Hohbach, Albritton, Test & Herbert

[57] ABSTRACT

Apparatus for being held by the human hand for performing refractive keratectomy on the eye of a patient by the use of radio frequency energy from a radio frequency generator. An elongate probe has proximal and distal extremities. The proximal extremity is sized to be grasped by a human hand. The elongate probe has a length so that the distal extremity can be held in close proximity to the cornea while the proximal extremity is held by the human hand. An energy delivery member is carried by the distal extremity. Conductors are carried by the elongate probe for conducting radio frequency from the generator to the energy delivery member. A dispersive member is carried by the energy delivery member for dispersing the radio frequency energy from the energy delivery member and applies the energy to the cornea to remove a portion of said cornea in order to reshape the cornea and improve vision.

26 Claims, 3 Drawing Sheets

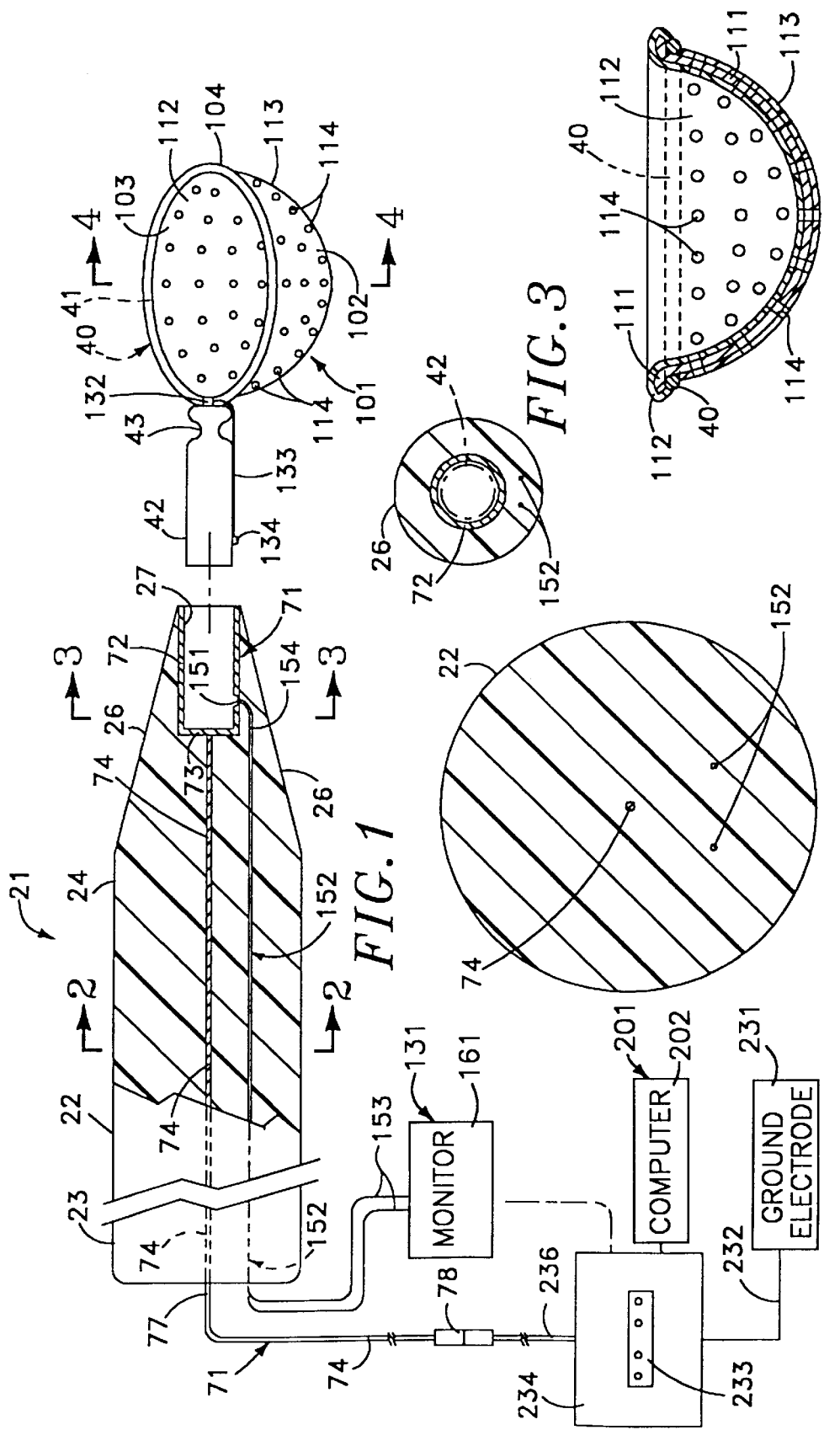

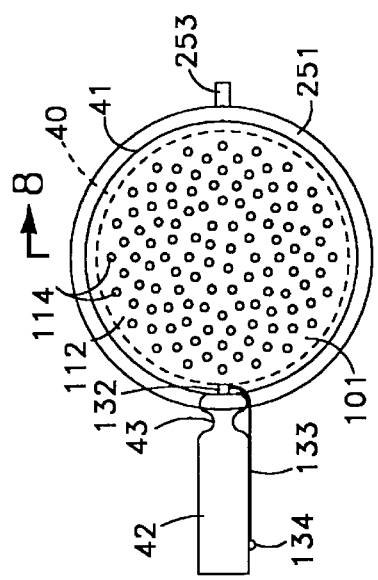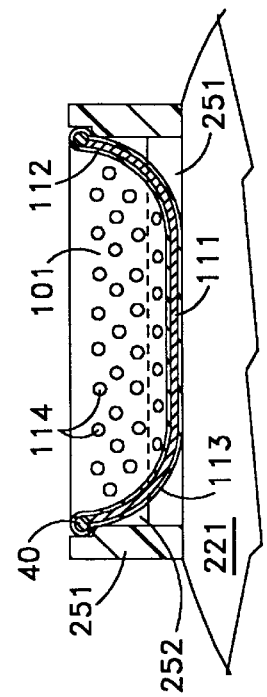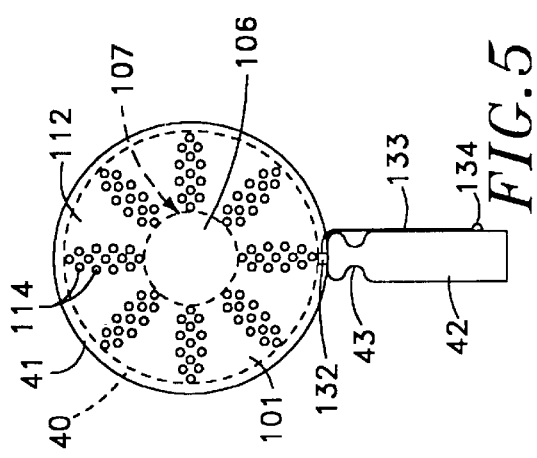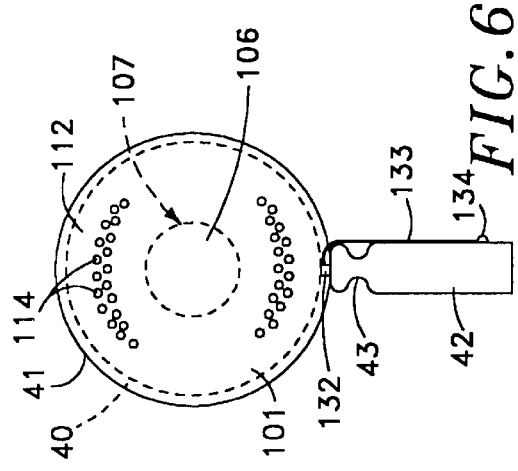

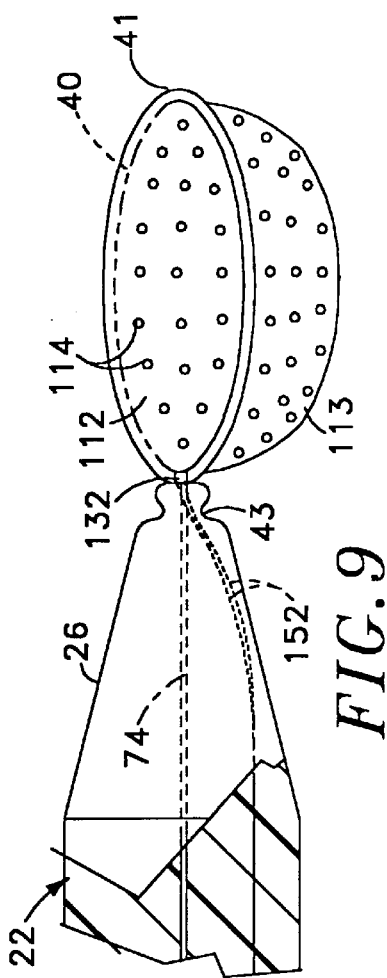
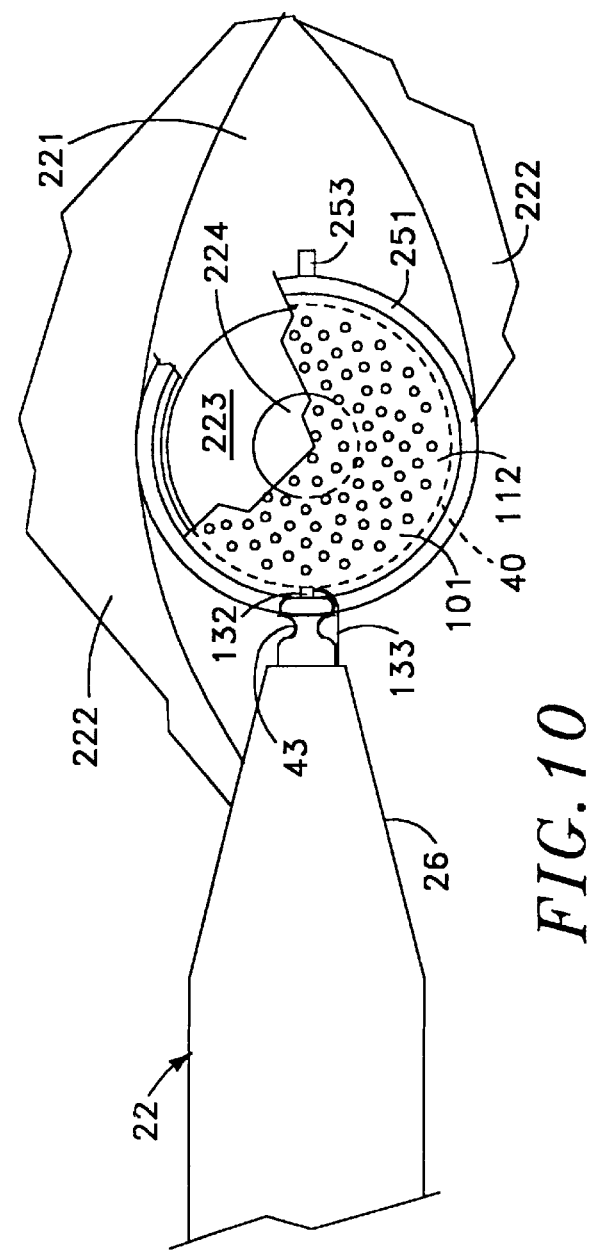

RADIO FREQUENCY REFRACTIVE KERATECTOMY APPARATUS AND METHOD

BACKGROUND OF THE INVENTION

This invention relates to a radio frequency energy refractive keratectomy apparatus and method for improving vision.

Optical impairment, due to ocular aberrations such as myopia, hyperopia, astigmatism, presbyopia and keratoconus, is a common problem. Adequate treatment of these conditions continues to present difficult challenges. Surgical and non-surgical remedies exist, none of which are ideal.

Refractive surgery encompasses a number of different procedures some of which are of historical interest only. Techniques include incisional keratotomy (IK) (including radial keratotomy (RK) and astigmatic keratotomy (AK)), photo-therapeutic keratectomy (PTK), thermokeratoplasty (TKP), photorefractive keratectomy (PRK), laser in situ keratomileusis (LASIK) and automated lamellar keratectomy (ALK). None of these procedures is without potential complications which can be visually debilitating. In addition, most techniques require high levels of expertise, unwieldy or extremely expensive equipment, or a combination thereof. Furthermore, no single technique has, of yet, been proven effective for treating all of the aforementioned optical aberrations. Accordingly, there is a need for an apparatus and method for improving vision by refractive keratectomy which addresses some of the aforementioned problems.

SUMMARY OF THE INVENTION

In general, it is an object of the present invention to provide a radio frequency energy refractive keratectomy apparatus and method in order to improve vision.

Another object of the invention is to provide an apparatus and method of the above character which applies radio frequency energy from a radio frequency generator to the cornea in order to reshape the cornea.

Another object of the invention is to provide an apparatus and method of the above character in which means for conducting radio frequency energy from a radio frequency generator and applying said radio frequency energy to the cornea is provided in order to reshape the cornea.

Another object of the invention is to provide an apparatus and method of the above character which utilize an energy delivery member in order to conduct radio frequency energy to the cornea.

Another object of the invention is to provide an apparatus and method of the above character which utilize loop electrodes having various shapes and sizes in order to conduct radio frequency energy to the cornea.

Another object of the invention is to provide an apparatus and method of the above character which utilize loop electrodes carrying energy conducting microporous members having various shapes and sizes in order to conduct radio frequency energy to the cornea.

Another object of the invention is to provide an apparatus and method of the above character wherein said loop electrode is frictionally, removably connectable to said distal extremity.

Another object of the invention is to provide an apparatus and method of the above character which provides means for monitoring and controlling the amount of energy applied to the cornea by monitoring the temperature at the cornea.

Another object of the invention is to provide an apparatus and method of the above character which provides means for controlling the amount of energy applied to the cornea based on the shape of the eye prior to applying said energy.

Another object of the invention is to provide an apparatus and method of the above character which provides means for dispersing and applying energy to the cornea in specific patterns.

Another object of the invention is to provide an apparatus and method of the above character which provides a corneal immobilizer with a vacuum chamber for substantially immobilizing the cornea during application of energy to the cornea.

Another object of the invention is to provide an apparatus and method of the above character which can be easily, quickly, safely and reliably used and does not require the concomitant administration of general anesthesia.

Another object of the invention is to provide an apparatus and method of the above character which is inexpensive and disposable.

Additional objects and features of the invention will appear from the following description in which the preferred embodiments and the methods using the same are described in conjunction with the accompanying drawings.

BRIEF DESCRIPTION OF THE DRAWINGS

FIG. 1 is an isometric view partially in section of an apparatus for radio frequency energy refractive keratectomy incorporating the present invention.

FIG. 2 is a cross-sectional view taken along the line 2—2 of FIG. 1.

FIG. 3 is a cross-sectional view taken along the line 3—3 of FIG. 1.

FIG. 4 is a cross-sectional view taken along the line 4—4 of FIG. 1.

FIG. 5 is a frontal plan view of another embodiment of the loop electrode and membrane of the present invention.

FIG. 6 is a frontal plan view of another embodiment of the loop electrode and membrane of the present invention.

FIG. 7 is a frontal plan view of another embodiment of the radio frequency keratectomy device of the present invention incorporating a corneal immobilizer.

FIG. 8 is a cross-sectional taken along the line 8—8 of FIG. 7.

FIG. 9 is an isometric view partially in section of another embodiment of the radio frequency keratectomy device of the present invention.

FIG. 10 is a frontal plan view depicting the eye with a radio frequency energy refractive keratectomy apparatus appropriately positioned over the cornea to apply radio frequency energy in order to reshape the cornea.

DETAILED DESCRIPTION OF THE INVENTION

In general, the apparatus of the present invention is held by the human hand and utilizes radio frequency energy from a radio frequency generator to reshape the cornea and thereby improve vision. The apparatus comprises an elongate probe having proximal and distal extremities, the proximal extremity being sized to be grasped by a human hand. The elongate probe has a length so that the distal extremity can be held in close proximity to the cornea while the proximal extremity is being held by the human hand. An energy delivery member is carried by the distal extremity and conductive means is carried by the elongate probe for conducting radio frequency energy from the generator to the energy delivery member. There is a dispersive member carried by the energy delivery member for dispersing the radio frequency energy from the energy delivery member and applying the energy to the cornea to remove a portion of the cornea in order to reshape the cornea and improve vision.

More specifically, as shown in FIGS. 1–10, the apparatus 21 of the present invention for reshaping the cornea consists of an elongate probe 22 or member formed of a suitable material such as plastic and constructed using any suitable method such as injection molding utilizing appropriate mandrils or by extrusion. The probe 22 has proximal and distal extremities 23 and 24 and is of a suitable shape, as by way of example, cylindrical or polygonally configured. The distal extremity 24 is provided with a tapered region 26 having an appropriate length which may be flat, cylindrically or polygonally configured. The elongate probe 22 is of a suitable size, as for example, having a diameter ranging from 0.5–2 cm, preferably approximately 1.25 cm, and a suitable length ranging from 10–40 cm, preferably approximately 15 cm.

The tapered region 26 of the distal extremity 24 of the elongate probe 22 is provided with a slot 27 or recess which is of a suitable configuration, as for example cylindrical, polygonal or rectangular, and has a length ranging from 0.5–7 cm, preferably approximately 2–3 cm, with a diameter ranging from 1–10 mm, preferably approximately 2.5 mm.

An energy delivery member, preferably in the form of a loop electrode 40, is provided and comprises a loop portion 41 and a shaft or stem portion 42 which shaft 42 portion is configured so as to be capable of being frictionally retained in the slot 27 of, and removably connected to, the distal extremity 24 of the elongate probe 22 as hereinafter described.

The loop 41 of the electrode 40 is, preferably circular in shape and is sized so as to encompass an area approximating the area of the cornea as hereinafter discussed. It should be appreciated that the loop 40 may also be elliptical in shape. Furthermore, various sizes and shapes of loop electrodes are provided to accommodate eyes and corneas of different shapes and sizes. In its original configuration, the loop 41 extends distal to the elongate probe 22. The electrode loop 41 is constructed of a suitable wire material such as a nickel-titanium having superelastic properties so that it will return to its original configuration after being bent as hereinafter described. The wire used to construct the loop 41 has a suitable diameter ranging from 0.002" to 0.040". It should be appreciated that any suitable, flexible, conductive material such as stainless steel or titanium can also be utilized to construct the loop 40.

The shaft portion 42 of the electrode 40 is made of a suitable material such as nickel-titanium or stainless steel and is suitably sized and configured so as to frictionally fit in the slot 27 of the elongate probe 22 as hereinbefore discussed. The loop 41 and shaft 42 portions of the electrode 40 are secured to one another by appropriate means such as by adhesive or solder joints. Preferably, the shaft 42 is constructed with a living hinge 43 situated at the distal portion of the shaft 42, immediately proximal to the point at which the shaft 42 and loop 41 portions of the electrode 40 are joined. Alternatively, the adhesive or solder joints can be constructed so as to function as a hinge connection between the loop 41 and the shaft 32.

Conductive means 71 is formed which includes the loop and shaft portions 41 and 42 of the electrode 40 and the slot 27 in the distal extremity 24 of the elongate probe 22 as hereinafter described. A liner 72, constructed of any suitable conductive material such as stainless steel or titanium, is retained within the slot 27 by appropriate means such as by being frictionally secured therein or adhesively bonded thereto. The liner 72 functions as a casing in which the shaft portion 42 of the electrode 40 is capable of being frictionally retained and by which conductive contact with the shaft portion 42 is established as hereinafter described. The proximal base 73 of the liner 72 is connected to a conducting wire 74 which is formed of a suitable conductive material and has a diameter ranging from 0.010" to 0.100". Preferably, the conducting wire 74 is embedded in the elongate probe 22, extends proximally therein and exits at an appropriate location on the proximal extremity 23 of the elongate probe 22. A portion of the conducting wire 77 extends proximally from the proximal extremity 23 of the probe 22 and is of an appropriate length so that it can be connected to a radio frequency generator as hereinafter described and the proximal end of the extending wire 77 carries an appropriate adaptor 78 therefor.

A microporous dispersive member 101 is carried by the loop portion 41 of the electrode 40 for dispersing radio frequency energy from the electrode 40 and applying the energy to the cornea as hereinafter described. The dispersive member 101 has a bag-like or sack-like conformation with a closed end 102 and an open end 103 forming a rim 104, the rim 104 being secured to the loop 41 in a suitable manner as by soldering or by a suitable adhesive. As such, dispersive members of various sizes are provided to be accommodated by various loops as hereinbefore discussed. The microporous member 101 includes a conductive layer 111 formed of a material capable of conducting radio frequency energy such as metal foil. When retained on the loop 41 of the electrode 40, the conductive layer 111 comes in contact with the electrode 40 at the rim 104 of the microporous member 101. The dispersive member 101 also includes first and second outer layers 112 and 113 formed of a material that is insulative with respect to radio frequency energy, as by way of example an elastic material like latex, the outer layers 112 and 113 being disposed on opposite sides of the conductive layer 111 to create a sandwiched configuration thereof. The conductive layer 111 and first and second outer layers 112 and 113 have micropores 114 therein in registration with one another. As shown with the embodiment in FIG. 1, the micropores 114 are distributed substantially randomly over the entire member 101. Alternatively, micropores may be disposed in a predetermined specific pattern as hereinafter described. When the apparatus of the present invention is used in conjunction with a conducting solution as hereinafter described, conducting solution delivered to the dispersive member 101 and thence to the micropores 114 flows through the microporous member 101 and assists in dispersing radio frequency energy from the loop 41 of the electrode 40 through said micropores 114 and applying said energy to the area of the cornea to be treated. The solution also serves to cool the surface of the cornea so as to prevent significant corneal heating resulting from the application of energy thereto.

Means 131 for monitoring and controlling the amount of radio frequency energy applied to the cornea is provided in the form of a thermocouple 132 carried by the loop electrode 40. Insulated shaft conductors 133 formed of an appropriate material and sized appropriately extend proximally from the thermocouple 132 and along the shaft 42 of the electrode 40 to which they are secured by appropriate means such as by an adhesive. The shaft conductors 133 may be connected to the thermocouple 132 by appropriate means, for example by being soldered. The proximal end of the shaft conductors 133 carry pins 134 or pegs as hereinafter described.

The proximal end of the casing or liner 72 carries two holes or apertures 151 which receive the pins 134 of the shaft conductors 133 when the shaft 42 is frictionally retained in the slot 27 of the distal extremity 24 of the elongate probe 22. Elongate probe conductors 152 having proximal and distal ends 153 and 154 are embedded in the elongate probe 22 during the injection molding or extrusion procedure and are disposed so that the distal ends 154 terminate at the surface of the slot 27 in the tapered portion 26 of the distal extremity 24 of the elongate probe 22 thereby contacting the apertures 151 in the casing 72 when the same is retainedly secured in the slot 27 and the pins 134 on the shaft conductors 133 when the pins 134 are retained in the apertures 151 as hereinbefore described.

The proximal ends 153 of the elongate probe conductors 152 extend out of the proximal extremity 23 of the elongate probe 22 an appropriate length so that they may be connected to a temperature monitoring device 161.

Means for monitoring and controlling the amount of energy applied to the cornea based on the shape of the eye 221 prior to applying said energy is provided by a computer 202 as hereinafter discussed. A patient's ophthalmological prescription (reflecting the shape of the globe as well as corneal topography prior to keratectomy)is programmed into the computer 202. A computer algorithm is then utilized to automatically adjust the amount of radio frequency energy applied to the cornea by varying the power and time of the same.

Operation and use of the apparatus 21 in performing the method of the present invention may now be described in conjunction with FIGS. 1–9. The anatomy of interest is partially shown and disclosed in FIG. 9 and consists of the eye 221, eyelids 222, cornea 223 and the pupil 224.

Let it be assumed that in anticipating use of this procedure, a patient's eyes have been previously evaluated and it has been ophthalmologically determined that the patient has imperfect vision. The present procedure is most appropriate for those patients in whom visual impairment is attributable to myopia, hyperopia or astigmatism.

Assuming that the patient's pretreatment evaluation warrants the use of radio frequency refractive keratectomy hereinafter described, the patient can be brought into the ophthalmologist's office, an outpatient clinic or an operating room in a hospital. The patient is placed either on an operating room table or in an ophthalmological examination chair which is capable of reclining. If the procedure is to be performed under general anesthesia then the necessary vital signs monitoring devices are applied to the patient and general anesthesia is induced. More typically, local anesthesia is utilized as hereinafter described. The patient's head is maintained in a neutral orientation so that, in a reclining position, the eye 221 to be treated is exposed and oriented upwardly or vertically. Either before or after positioning the patient, a conventional indifferent or neutral grounding electrode 231 is placed on the patient's upper back or upper arm so that it is adherent thereto and makes good electrical contact with the skin of the patient. If both eyes are to be treated, the electrode is, preferably placed on the patient's upper mid back. The electrode 231 is connected by an electrical cable 232 into a control console 233 and radio frequency generator 234. The control console 233 is provided with appropriate digital readouts thereon. A foot switch may be connected by cable into the control console for controlling or activating the application of radio frequency power as hereinafter described.

Typically, the radio frequency generator 234, temperature monitor 161, computer 202 and all cables thereto are maintained and available in the aforementioned locations where the patient is to be treated and are of the reusable type. Only the elongate probe 22, electrode 40 and dispersive member 101 would be considered to be disposable after use on a single patient. Thus, in preparation for the procedure, an ophthalmological exam is repeated, preferably with a phoropter and slit lamp and with review of data obtained from a video keratometer examination performed earlier, in order to re-assess the eye 221 to be treated and in order to select an elongate probe 22 with an appropriately sized and shaped loop electrode 40. In addition, the patient's ocular prescription, or similar data determined from the eye examination, is programmed into the computer 202 so that the computer algorithm is initiated and the computer 202 automatically selects the power level and duration of radio frequency energy to be applied to the cornea 223 as hereinafter described. The elongate probe 22 is connected to the radio frequency generator 234 and the temperature monitor 161 by connecting the wire 74, extending from the proximal extremity 23 of the elongate probe 22, and its adaptor 78 to the cable 236 into the control console 233. The computer 202 and temperature monitor 161 are connected to the control console 233 by appropriate means.

To administer local anesthesia, the physician introduces a conventional ophthalmological anesthetic solution such as tetracaine or marcaine drops into the eye 221 to be treated. After this has been accomplished, the physician may immobilize the eyelids 222 in the open position in order to provide surgical exposure by utilizing a conventional, spring-loaded eyelid retractor 237. In addition, a conventional corneal mask may be used to block the portion of the cornea that is not to be remodeled as is well known to those skilled in the art. This is not necessary however, inasmuch as the microporous member 101 functions in much the same manner as a corneal mask by covering the portion of the cornea 223 which is not supposed to receive energy with insulating material.

With one hand, the physician places the distal extremity 24 of the elongate probe 22 with the loop electrode 40 and the dispersive member 101 onto the cornea 223 of the eye 221 to be treated until the dispersive member 101 is substantially centered over the cornea. A conducting solution, such as 0.9–5% saline and preferably normal saline, is liberally applied onto the dispersive member 101 and the eye 221 by any suitable means. This is usually accomplished with the use of a conventional ophthalmological drip bottle held by the physician in his second hand or by an assistant. The saline solution not only assists in energy conduction but also serves to cool the surface of the cornea so that the underlying corneal stromal layer is preferentially heated.

After these procedures have been accomplished, the patient is ready to have radio frequency energy supplied to the loop electrode 40, the dispersive microporous member 101 and thus, via the micropores 114, to the cornea 223. Radio frequency energy is supplied from the control console 233 and radio frequency generator 234 in conjunction with the computer controller 202. Preferably, activation of the computer algorithm causes radio frequency energy of the predetermined, pre-programmed and desired frequency and power level to be supplied to the loop 41 of the electrode 40 disposed adjacent to the cornea 223 for a predetermined period of time. The computer algorithm may provide for continuous application of said energy or pulsatile application thereof.

Typically, the radio frequencies can range from 300 kHz to 10 mHz although frequencies approximating 500 kHz are utilized.

The radio frequency energy is applied in two brief stages in the same sitting. Prior to both stages, the patient is instructed to look straight ahead and attempt to keep the eye to be treated as motionless as is possible. The first stage involves epithelial removal, akin to the photo therapeutic keratectomy done prior to photorefractive keratectomy. For the first stage the dispersive member 101 having a substantially random distribution of micropores 114 is utilized. The second stage involves radio frequency energy application to effect the refractive keratectomy. The same dispersive member 101 may be utilized or, alternatively, a dispersive member having a predetermined specific pattern may be used as hereinafter described. The two stages also generally differ not only in the choice of dispersive members used but in the duration of energy application.

The radio frequency energy is delivered at relatively low power levels ranging from 1–10 watts. The duration of application of radio frequency energy can vary depending on the patient's corneal anatomy, however, typically a total period of 0.25 to 30 seconds is appropriate. Typically, for the first, epithelial removal stage, 15 seconds is usually adequate. For the refractive stage of energy application, the computer algorithm selects these variables based on pre-treatment ocular shape as hereinbefore discussed. By way of example, initial power could be delivered at 2 watts for 5 seconds.

With the brief applications of radio frequency energy utilized in the method of the present invention, temperature elevations in corneal tissue are minimal and immeasurable. Nonetheless, at a microscopic tissue level, a temperature rise occurs as hereinafter described. It should be appreciated that the radio frequency generator 234 and control console 233 are provided with controls which will automatically shut off the application of RF power in the event excessive temperatures (as set by the physician) are sensed by the thermocouple 132.

The use of low voltage, low frequency, low power radio frequency energy permits corneal tissue volume reduction of the targeted area while preserving surrounding tissue and structures. In other words, by controlling the application of radio frequency energy to the cornea 223 treatment can be effected while preserving the integrity of the cornea 223 and other surrounding structures of the eye 221. It is well established that human cells die as a result of being desiccated if exposed to temperatures above 47 degrees centigrade for a few seconds. Thus, the treating temperature achieved has to exceed 47 degrees, at least at the cellular level of the small portion of corneal tissue being ablated. To avoid carbonization of the same cells and damage to additional cells and surrounding tissue however, the temperature should be maintained at less than 100 degrees centigrade. Published data confirms that an output of 8 watts during a period of six seconds will raise the tissue temperature to 55 degrees centigrade, while 10 watts applied for six seconds will raise the temperature to 82 degrees centigrade. Saline applied to the eye 221 and the microporous dispersive member 101 helps conduct the RF energy to predetermined portions of the cornea while also serving as a buffer to prevent undue temperature elevation thereat. As hereinbefore described, by monitoring the cornea 223 temperature during treatment, the thermocouple 132 on the loop electrode 40 also to serves to prevent excessive tissue destruction resulting from undue heating thereof. The controlled, thermic desiccation of cells forms microscopic necrotic lesions which are absorbed within days while the adjacent tissue gently shrinks. By creating the corneal lesions in locations that are predetermined, based on a patient's pre-treatment ocular anatomy, the cornea 223 is predictably reshaped and vision thereby improved.

After terminating the radio frequency application, the physician may choose to instill antibiotic drops into the treated eye. A protective soft contact lens may also be placed on the treated eye. The patient is returned to a full upright position, observed for a brief period of time and thereafter permitted to leave the treatment area. If necessary, upon follow-up examination it may be determined that additional radio frequency energy application should be undertaken to further reshape a cornea upon which RF keratectomy has been performed. Staged procedures can thus be employed to gently and more precisely reshape the cornea as necessary.

Another embodiment of the dispersive member which is similar to that disclosed in FIG. 1 is shown in FIG. 5. Thus, all parts of the dispersive member shown in FIG. 5 carry the same numbers as the dispersive member in FIG. 1. In the dispersive member 101 shown in FIG. 5, the micropores 114 are disposed in a predetermined specific pattern. Inasmuch as the cornea 223 possesses a central optical zone which corresponds approximately to the maximum pupillary size, the microporous dispersive member 101 has a central region 106 having a circumference 107 sized so as to encompass an area approximating the area of said optical zone. Specifically, the pattern of micropores 114 includes a substantially radial array thereof, having spoke-like clusters of said micropores 114 radiating from said circumference 107. There are at least two spoke-like clusters 114 and, preferably, can be eight or more spoke-like clusters.

Operation and use of the dispersive member 101 shown in FIG. 5 is similar to that described hereinbefore in conjunction the apparatus shown in FIG. 1. With corneal application of RF energy being localized to the radially arrayed micropores 114, the resultant desiccation creates lesions in a pattern similar to those created by traditional radial keratotomy incisions which spare the optical zone of the cornea 223.

Another embodiment of the dispersive member which is also similar to that disclosed in FIG. 1 is shown in FIG. 6. Thus, all parts of the dispersive member shown in FIG. 6 carry the same numbers as the dispersive member in FIGS. 1 and 5. In the dispersive member 101 shown in FIG. 6, the micropores 114 are also disposed in a predetermined specific pattern. The specific pattern includes at least one curvilinear cluster of said micropores 114 disposed outside of the central region 106. This pattern results in a desiccation pattern similar to that created by traditional astigmatic keratotomy incisions.

Another embodiment of the apparatus of the present invention is shown in FIGS. 7–8. It is similar to the apparatus shown in FIG. 1 and thus, all similar parts of the apparatus carry the same numbers as in FIG. 1. In addition, the apparatus carries a corneal immobilizer 251 for substantially immobilizing the cornea 223 during application of RF energy thereto. The corneal immobilizer 251 is constructed of a suitable insulative material, such as plastic, and is secured to the rim 104 of the loop portion 41 of the electrode 40 in any appropriate manner, such as by using an adhesive. Alternatively, the corneal immobilizer 251 may also be passively set on the eye 221, separately from the dispersive member 101, in which case the dispersive member 101 is retained within the immobilizer 251 as hereinafter described. The immobilizer 251 is of an appropriate size and shape, preferably circular, so that it conforms to and is slightly larger than the dispersive member 101. It carries an annular inwardly extending flange 254 so that the rim 104 of the dispersive member 101 is retained within the immobilizer 251. The corneal immobilizer 251 also includes a vacuum chamber 252 and at least one external vacuum attachment 253 located below the level of the portion of the immobilizer 251 in which the dispersive member 101 is seated. The vacuum attachment 253 is capable of being connected to a vacuum source for applying suction to the eye 221 in order to immobilize the eye 221 during the refractive keratectomy procedure.

Operation and use of the apparatus 21 is similar to that hereinbefore disclosed in conjunction with the apparatus shown in FIG. 1. The corneal immobilizer 251 is placed on the eye 221 and secured thereto by connecting a conventional low pressure vacuum source to the vacuum attachments 253 on the vacuum chamber 252 of the corneal immobilizer 251. Application of suction to the immobilizer 223 gently secures the immobilizer 251 to the conjunctivae of the eye 221 and, in so doing, brings the cornea 223 into operative contact with the dispersive member 101. It should be appreciated that with the use of the corneal immobilizer 251, eyelid retractors are unnecessary. The remainder of the procedure is as hereinbefore described in conjunction with the apparatus shown in FIG. 1.

Another embodiment of the apparatus of the present invention is shown in FIG. 9. It is similar to the apparatus shown in FIG. 1 and thus, all similar parts of the apparatus carry the same numbers as in FIG. 1. The distal extremity 24 of the elongate probe 22 of the embodiment shown in FIG. 9 carries an electrode 40 that is secured to the distal extremity 24 and is, therefore, without shaft and casing portions. Rather, the electrode 40 is, preferably, secured to the distal extremity 24 by forming the loop 41 from a continuous conducting wire 74 which is embedded proximally in the elongate probe 22 as hereinbefore described, thereby also forming a hinge connection 43 between the electrode 40 and the distal extremity 24 of the elongate probe 22. Alternatively, the loop electrode can be a separate portion of wire secured to the distal extremity 24 of the probe 22 by a suitable adhesive, the distal extremity 24 of the probe 22 including a living hinge 43 formed during construction of the probe 22. The loop 41 is closed by appropriate means, as by way of example, with solder or an appropriate adhesive. The rim 104 of the dispersive member 101 is frictionally retained on the loop portion 41 of the electrode 40. As such, various dispersive members may be interchanged on the electrode 40 for different portions of the radio frequency keratectomy procedure as hereinbefore described.

Operation and use of the apparatus disclosed in FIG. 9 is similar to that hereinbefore described.

It should be appreciated that other embodiments are encompassed by the apparatus of the present invention. A bi-polar radio frequency elongate probe may be constructed which comprises an active electrode carried by the distal end of the probe, a return electrode carried by the shaft of the probe and an insulated portion therebetween. During operation of such a bi-polar probe, immersion in a conductive solution permits RP current to flow from the active electrode to the return electrode, thus obviating the traditional bi-polar electrode requirement that the return electrode be in contact with the active electrode in order for current to flow. In addition, only tissue in contact with the active electrode has current pass therethrough thereby preserving other advantages of bi-polar radio frequency application.

It is apparent from the foregoing that there has been provided a novel apparatus and method for refractive keratectomy using radio frequency energy. The procedure can be used for reshaping the cornea of a myopic, hyeropic or astigmatic eye, thus improving vision for patients with a variety of visual impairments. As a result of employing computer programmed, pre-determined patterns and degrees of radio frequency energy application based on a patient's pre-procedure ocular prescription, corneal topography is optimally reshaped and reconfigured in a selective and controlled manner such that vision is restored as closely as possible to 20—20, thus obviating the need for contact lenses and glasses in many people. The concomitant monitoring of temperature and further regulation of energy application based thereon provides an additional safety margin so that corneal integrity is maintained and neither it nor surrounding ocular tissues are damaged during the procedure. There is no bleeding, no requirement for general anesthesia, the procedure is brief and the potential for complications, such as pain and infection, minimal. In addition the apparatus and method of the present invention provide an inexpensive, simpler and less unwieldy alternative to laser keratectomy.

What is claimed:

1. Apparatus for being held by the human hand for performing refractive keratectomy on the eye of a patient by the use of radio frequency energy from a radio frequency generator comprising an elongate probe having proximal and distal extremities, the proximal extremity being sized to be grasped by a human hand and the elongate probe having a length so that the distal extremity can be held in close proximity to the cornea while the proximal extremity is being held by the human hand, an energy delivery member carried by the distal extremity, conductive means carried by the elongate probe for conducting radio frequency from the generator to said energy delivery member and a dispersive member carried by said energy delivery member for dispersing the radio frequency energy from the energy delivery member and applying said energy to the cornea to remove a portion of said cornea in order to reshape the cornea and improve vision.

2. An apparatus as in claim 1 wherein said energy delivery member is a loop electrode.

3. An apparatus as in claim 2 wherein said loop electrode is sized so as to encompass an area approximating the area of the cornea.

4. An apparatus as in claim 2 wherein said loop electrode is removably connectable to said distal extremity.

5. An apparatus as in claim 2 wherein said dispersive member is microporous.

6. An apparatus as in claim 5 wherein said microporous member has a bag-like conformation with a closed end and an open end forming a rim.

7. An apparatus as in claim 6 for use with a conductive solution wherein said microporous member includes a conductive layer formed of a material capable of conducting radio frequency energy, said conductive layer being in contact with the loop electrode at said rim of said microporous member, first and second outer layers formed of a material that is insulative with respect to radio frequency energy and disposed on opposite sides of the conductive layer and wherein said conductive layer and said first and second outer layers have micropores therein in registration with one another permitting a conducting solution to flow through said microporous member to assist in dispersing the radio frequency energy from said loop electrode through said micropores and applying said energy to the area of the cornea to be reshaped.

8. An apparatus as in claim 7 wherein said conductive layer is constructed of metal foil.

9. An apparatus as in claim 7 wherein said outer layers are constructed of an elastic material.

10. An apparatus as in claim 7 wherein said micropores are disposed in a predetermined specific pattern.

11. An apparatus as in claim 10, the cornea having a central optical zone, wherein said microporous member has a central region sized so as to encompass an area approximating the area of said optical zone and said specific pattern includes at least one curvilinear cluster of said micropores disposed outside of said central region.

12. An apparatus as in claim 10, the cornea having a central optical zone, wherein said microporous member has a central region having a circumference sized to encompass an area approximating the area of said optical zone and said specific pattern is a substantially radial array having spoke-like clusters of said micropores radiating from said circumference.

13. An apparatus as in claim 12 wherein there are at least two spoke-like clusters.

14. An apparatus as in claim 13 wherein there are eight spoke-like clusters.

15. An apparatus as in claim 7 wherein said dispersive member is removably connectable to said distal extremity.

16. An apparatus as in claim 1 further including means for monitoring and controlling the amount of radio frequency energy applied to the cornea.

17. An apparatus as in claim 16 wherein said monitoring and controlling means includes a computer for controlling the amount of energy applied to the cornea based on the shape of the eye prior to applying said energy.

18. An apparatus as in claim 16 wherein said monitoring and controlling means includes at least one thermocouple carried by said energy delivery member.

19. An apparatus as in claim 1 further including a corneal immobilizer for substantially immobilizing the cornea during application of said energy.

20. An apparatus as in claim 19 wherein the corneal immobilizer includes a vacuum chamber capable of being connected to a vacuum source for applying suction to the eye.

21. A method for performing refractive keratectomy on the eye of a patient, the cornea having a central optical zone, by the use of radio frequency energy and an apparatus having an elongate probe being sized to be grasped by a human hand, an energy delivery member carried by the elongate probe and a dispersive member carried by said energy delivery member for dispersing the radio frequency energy, the method comprising placing said dispersive member on the eye so that the energy delivery member and dispersive member contact the cornea, introducing a conducting solution onto the eye so that it contacts said dispersive member and conducting radio frequency energy to said energy delivery member, said dispersive member and to an area of the cornea to ablate a portion of the cornea in order to reshape the cornea and improve vision.

22. A method as in claim 21 wherein said energy is conducted to an area of the cornea located outside of the optical zone.

23. A method as in claim 21 wherein said energy is conducted to an area of the cornea including the optical zone.

24. A method as in claim 21 further including the steps of monitoring the temperature at the cornea during application of energy to the cornea and controlling the amount of energy applied to the cornea based on the temperature.

25. A method as in claim 21 further including the step of controlling the amount of energy applied to the cornea based on the shape of the eye prior to applying said energy.

26. A method as in claim 21, the apparatus further including a corneal immobilizer having a vacuum chamber capable of being connected to a vacuum source, including the steps of applying the corneal immobilizer to the eye of the patient and applying a vacuum source to the corneal immobilizer in order to immobilize the cornea prior to introducing said conducting solution.

* * * * *